United States Patent
Yuen et al.

(10) Patent No.: US 11,357,751 B2
(45) Date of Patent: Jun. 14, 2022

(54) COMPOSITION FOR PREVENTING OR MITIGATING DEMENTIA

(71) Applicant: Attest Research Sdn Bhd, Ipoh (MY)

(72) Inventors: Kah Hay Yuen, Ipoh (MY); David Sue San Ho, Ipoh (MY); Jia Woei Wong, Ipoh (MY)

(73) Assignee: Attest Research Sdn Bhd, Ipoh (MY)

( * ) Notice: Subject to any disclaimer, the term of this patent is extended or adjusted under 35 U.S.C. 154(b) by 100 days.

(21) Appl. No.: 16/304,248

(22) PCT Filed: Aug. 17, 2016

(86) PCT No.: PCT/MY2016/050046
§ 371 (c)(1),
(2) Date: Nov. 23, 2018

(87) PCT Pub. No.: WO2017/204618
PCT Pub. Date: Nov. 30, 2017

(65) Prior Publication Data
US 2020/0316017 A1    Oct. 8, 2020

(30) Foreign Application Priority Data
May 23, 2016 (MY) ............... PI 2016701846

(51) Int. Cl.
*A61K 31/355* (2006.01)
*A61K 31/01* (2006.01)
*A61K 31/519* (2006.01)
*A61K 31/675* (2006.01)
*A61K 31/714* (2006.01)

(52) U.S. Cl.
CPC ............ *A61K 31/355* (2013.01); *A61K 31/01* (2013.01); *A61K 31/519* (2013.01); *A61K 31/675* (2013.01); *A61K 31/714* (2013.01)

(58) Field of Classification Search
None
See application file for complete search history.

(56) References Cited

U.S. PATENT DOCUMENTS

| 8,586,109 B2 * | 11/2013 | Tan ............... A61K 36/889 424/727 |
| 2009/0110745 A1 | 4/2009 | Shea et al. |
| 2011/0201679 A1 * | 8/2011 | Rubin ............ A61K 31/355 514/456 |
| 2012/0148685 A1 * | 6/2012 | Rohner ........... A61K 36/82 424/727 |
| 2016/0235794 A1 * | 8/2016 | Leclere-Bienfait ....... C11B 3/02 |

FOREIGN PATENT DOCUMENTS

| DE | 4326675 A1 * | 2/1995 | ...... A61K 31/714 |
| ES | 2517741 | 11/2014 | |
| ES | 2517741 A1 * | 11/2014 | ...... A61K 31/197 |
| WO | WO-2007034323 A1 * | 3/2007 | ...... A61K 31/4406 |
| WO | 2014025905 | 2/2014 | |
| WO | 2015050430 | 4/2015 | |

OTHER PUBLICATIONS

Mata et al. ES2517741 Composition to reduce and/or prevent hair loss and/or stimulate hair growth, 2014, machine translation obtained from https://worldwide.espacenet.com (Year: 2014).*
Chuang, M. H., & Brunner, G. (2006). Concentration of minor components in crude palm oil. The Journal of supercritical fluids, 37(2), 151-156. (Year: 2006).*
English Abstract of ES 2517741.
Cheruvanky, R., "Phytochemical Products: Rice Bran," Phytochemical Functional Foods, 2003, Editors: Johnson, Ian; Williamson, Gary. Publisher: CRC Press, Boca Raton, USA, pp. 347-376.
Gopalan, Y. et al., "Clinical Investigation of the Protective Effects of Palm Vitamin E Tocotrienols on Brain White Matter," Stroke, 2014, vol. 45, No. 5, pp. 1422-1428.
International Search Report dated Nov. 1, 2016.
Written Opinion of the International Searching Authority dated Nov. 1, 2016.
International Preliminary Report on Patentability dated May 2, 2018.

* cited by examiner

*Primary Examiner* — Dale R Miller
(74) *Attorney, Agent, or Firm* — Preston Smirman; Smirman IP Law, PLLC

(57) ABSTRACT

The present invention provides a composition for preventing or mitigating dementia in a subject comprising a mixture of tocotrienols, tocopherol, squalene and B vitamin, and a pharmaceutically acceptable carrier.

3 Claims, No Drawings

COMPOSITION FOR PREVENTING OR MITIGATING DEMENTIA

CROSS-REFERENCE TO RELATED APPLICATION

The instant application is a national phase of PCT International Patent Application Serial No. PCT/MY2016/050046 filed Aug. 17, 2016, and claims priority to Malaysia Patent Application Serial No. PI 2016701846 filed May 23, 2016, the entire specifications of both of which are expressly incorporated herein by reference.

FIELD OF INVENTION

The present invention relates to a composition for preventing or mitigating dementia. More particularly, it comprises a mixture of tocotrienols, tocopherols, and B vitamins.

BACKGROUND OF THE INVENTION

Globally, the proportion of older person in the total population is rising rapidly since the mid-twentieth century. It is projected that the proportion of the world's population over 60 years old will nearly double from 12% to 22% between 2015 and 2050. Population ageing is taking place almost everywhere, but its extent and speed varies among countries and between regions. It has been shown that population ageing has started in most of the developed nations and was beginning to take place in some developing countries. The proportion of the population aged 60 years or above in the more developed regions was 12% in 1950, rose to 23% in 2013 and is expected to reach 32% in 2050. In the less developed regions and least developed regions, the proportion of older persons is expected to reach 19% and 10%, respectively, in 2050.

The advances in public health and medicine contribute to extended life expectancy. Whilst most of the elderly have good mental health, a significant number of them are at risk of developing or has developed chronic diseases and disability such as mental disorders, neurological disorders, diabetes, osteoarthritis and loss of hearing. Among the principal health threats to the elderly are cognitive impairment and dementia, whose incidence and prevalence increases sharply with age. The most common neuropsychiatric disorder in the age group of 60 or above is dementia. About 5 to 8 in 100 people who aged 60 years or above develop dementia. In the world population, there are about 47.5 million people diagnosed with dementia, and 7.7 million new cases are recorded every year. Due to the progressive aging of the population, it is estimated that the number of elderly with dementia will triple in 2050.

Dementia is a clinical syndrome in which there is a deterioration in memory, thinking, behavior and the ability to perform daily activities beyond what might be expected from normal ageing. It can be categorized into three stages: the early stage, middle stage and late stage. The early stage of dementia is characterized by forgetfulness and losing track of time, which are often overlooked as the onset is gradual. When the disorder progresses, the symptoms become clearer. Elderly at the middle stage of dementia become forgetful of recent events and people's name, and have the tendency of becoming lost at home and repeatedly questioning. Memory disturbances are serious at the late stage of dementia. The demented elderly become unaware of the time and place and having difficulty in recognizing people. They also have difficulty in walking, thus increasing their need for assisted self-care.

The physical, emotional and economic pressures of this disorder can cause great stress to families. Therefore, there is an urgent need for strategies to prevent or delay the onset of dementia and slow down the progression in older person.

The present invention provides a composition for preventing or mitigating dementia.

SUMMARY OF THE INVENTION

The primary object of the invention is to provide a composition for preventing or mitigating dementia comprising tocotrienols, tocopherols and B vitamins.

Another object of the invention is to provide a composition for preventing or mitigating dementia which is capable of preventing or delaying the progression of white matter lesions which is one of the most significant pathological findings in individuals with dementia.

At least one of the preceding objects is met, in whole or in part, by the present invention, in which the embodiment of the present invention describes a composition for preventing or mitigating dementia in a subject comprising a mixture of tocotrienols, tocopherols, squalene, and B vitamins, and a pharmaceutically acceptable carrier.

More particularly, the tocotrienols can be any one or any combination of alpha-tocotrienol, beta-tocotrienol, gamma-tocotrienol and delta-tocotrienol. The tocopherol in the composition can be alpha-tocopherol. Preferably, tocotrienols are present in an amount of ranging from 15% to 35% by weight of the composition whereas tocopherols are present in an amount of ranging from 3% to 9% by weight of the composition.

Squalene derived from plant is preferred in the composition disclosed herein. Preferably, squalene is present in an amount of 1.0% to 5.0% by weight of the composition.

In the composition disclosed herein, the B vitamins can be any one or any combination of vitamin B6, vitamin B9 and vitamin B12. B vitamins are present in an amount of ranging from 0.5% to 10.5% by weight of the composition.

The pharmaceutically acceptable carrier suitable for use in the composition is any one or any combination of plant-based oil, caprylocaproyl macrogolglycerides, polyoxyethylene castor oil derivatives, polysorbate, polyglycerol esters of fatty acids, sucrose esters of fatty acids, polyethylene alkyl esters, polyoxyl 40 stearate and phospholipids. The pharmaceutically acceptable carrier is present in an amount of ranging from 24% to 80% by weight of the composition.

The present invention also provides a composition for preventing or mitigating dementia in a subject comprising 4% to 11% by weight of alpha-tocotrienol, 0.25% to 2% by weight of beta-tocotrienol, 7% to 15% by weight of gamma-tocotrienol, 2.0% to 7% by weight of delta-tocotrienol, 3% to 9% by weight of alpha-tocopherol, 1.0% to 5.0% by weight of squalene, 0.5% to 10.0% by weight of vitamin B6, 0.01% to 0.1% by weight of vitamin B9, 0.01% to 0.1% by weight of vitamin B12, and 24% to 80% by weight of a pharmaceutically acceptable carrier.

DETAILED DESCRIPTION OF THE INVENTION

One skilled in the art will readily appreciate that the present invention is well adapted to carry out the objects and obtain the ends and advantages mentioned, as well as those inherent therein. The embodiment described herein is not intended as limitations on the scope of the invention.

The present invention discloses a composition for preventing or delaying dementia in a subject comprising a mixture of tocotrienols, tocopherol, squalene, and B vitamins, and a pharmaceutically acceptable carrier. Particularly, the composition is able to prevent or delay the onset of dementia in the subject. The term "dementia" as used herein refers to chronic and progressive disorder of the mental functions caused by brain disease or injury. It is characterized by gradual decline of the brain functions which includes some or all, but not limited to the following characteristics: memory loss, language impairment, disorientation, changes in personality, difficulties with daily activities, self-neglect and psychiatric symptoms. There are many types of dementia due to various causes and diseases and these include, but not limited to Alzheimer's disease, vascular dementia, and dementia with Lewy bodies, frontotemporal dementia, Picks Disease, mixed dementias, dementia due to Parkinson's disease, Creutzfeldt-Jakob disease, normal pressure hydrocephalus, Huntington's disease, Wernicke-Korsakoff Syndrome, traumatic brain injury, Down syndrome, HIV-related neurocognitive disorder, mild cognitive impairment, posterior cortical atrophy, corticobasal degeneration, multiple sclerosis, Niemann-Pick disease type C, progressive supranuclear palsy, argyrophilic grain disease, cerebral autosomal dominant arteriopathy with subcortical infarcts and leukoencephalopathy (CADASIL), Binswanger's disease, young onset dementia, multi-infarct dementia and alcohol-related dementia. In more particular, the composition disclosed herein is able to prevent, delay or mitigate memory deterioration and/or other mental abilities.

Accordingly, the composition comprises tocotrienols and tocopherol. In the preferred embodiment of the invention, the tocotrienols is any one or any combination of alpha-tocotrienol, beta-tocotrienol, gamma-tocotrienol and delta-tocotrienol. More preferably, the composition comprises alpha-tocotrienol, beta-tocotrienol, gamma-tocotrienol and delta-tocotrienol. In the composition disclosed herein, tocotrienols constitute about 10% to 40%, or more preferably 15% to 35%, by weight of the composition. The preferred tocopherol used in the composition is alpha-tocopherol. Tocopherol may present in the composition in an amount of ranging from 1% to 15% by weight of the composition. More preferably, it is present in an amount ranging from 3% to 9% by weight of the composition.

Tocotrienols and tocopherol in the composition attenuate the progression of the white matter lesions (WMLs) volume in the brain. WMLs refer to the abnormal hyperintense regions in the brain observed during a magnetic resonance imaging (MRI). They are attributed to degeneration of small blood vessel in the brain, leading to chronic hypoperfusion and ischemic damage in the white matter. WMLs are progressive in nature. The presence of WMLs in the brain is associated with a higher risk of dementia and impairment in cognitive functions in demented and non-demented persons. Therefore, since the composition disclosed herein can impede the increase in the volume of MWLs in the brain, it is able to prevent or delay the onset d dementia as well as mitigate the progression of dementia.

Furthermore, tocotrienols and tocopherol possess neuroprotective properties. Tocotrienols block glutamate-induced c-Src and 12-lipoxygenase activation which contribute to neuronal cell death. Moreover, tocotrienols and tocopherol reduce oxidative stress which is involved in the pathogenesis and progression of dementia, particularly in Alzheimer's disease. They also preserve endothelial cell functions, inhibit platelet aggregation and serotonin release, and modulate protein kinase C signal transduction Inflammation, which is an important factor associated with dementia, can be attenuated by tocotrienols and tocopherol. The neuroprotective properties of tocotrienols and tocopherol provide the composition disclosed herein the ability to prevent or delay the onset of dementia.

In addition to tocotrienols and tocopherol, the composition also comprises squalene. Preferably, plant-based squalene is used in the composition. Sources of plant-based squalene include, but not limited to, olive, oil palm fruits, amaranth seed, and rice bran. Similar to tocotrienol and tocopherol, squalene possesses anti-oxidant and anti-inflammatory activities which can lead to a halt in the progression of memory deterioration. Preferably, squalene constitutes 1% to 10% by weight of the composition. More preferably, it constitutes 1% to 5% by weight of the composition.

Accordingly, the composition further comprises B vitamins. Pursuant to the preferred embodiment of the invention, B vitamins in the composition can be any one or any combination of vitamin B6, vitamin B9 and vitamin B12. Preferably, the B vitamin is present in an amount of ranging from 0.1% to 15%, or more preferably 0.5% to 10.5%, by weight of the composition. B vitamins are able to slow down the rate of brain degeneration in individuals with mild cognitive impairment (MCI) which are at risk of developing dementia. They can also reduce oxidative stress in brain cells. Moreover, B vitamins prevent increase in white matter hyperintensity burden by lowering the level of homocysteine in bloodstream. Hence, the composition disclosed herein is able to prevent the onset of dementia.

In a further embodiment of the invention, the composition may comprise beeswax and/or butylated hydroxytoluene. Beeswax is a suspending agent. It suspends tvitamin B powder in the pharmaceutically acceptable carrier, particularly oil-based carrier, in order to facilitate the encapsulation of the composition. Butylated hydrotoluene is an anti-oxidant. It helps to stabilize the tocotrienols in the capsules.

In accordance with the preferred embodiment of the invention, the pharmaceutically acceptable carrier is any one or any combination of plant-based oil, caprylocaproyl macrogolglycerides, polyoxyethylene castor oil or derivatives, polysorbate, polyglycerol esters of fatty acids, sucrose esters of fatty acids, polyethylene alkyl esters, polyoxyl 40 stearate and phospholipids. More preferably, the pharmaceutically acceptable carrier is plant-based oil, caprylocaproyl macrogolglycerides, polyoxyethylene castor oil or derivatives, or any combination thereof. In the composition disclosed herein, the pharmaceutically acceptable carrier is present in an amount of ranging from 20% to 90% by weight of the composition. In a more preferred embodiment, the pharmaceutically acceptable carrier is present in an amount of ranging from 24% to 80% by weight of the composition.

The present invention also describes a composition for preventing or mitigating dementia in a subject comprising 4% to 11% by weight of alpha-tocotrienol, 0.25% to 2% by weight of beta-tocotrienol, 7% to 15% by weight of gamma-tocotrienol, 2.0% to 7% by weight of delta-tocotrienol, 3% to 9% by weight of alpha-tocopherol, 1.0% to 5.0% by weight of squalene, 0.5% to 10.0% by weight of vitamin B6, 0.01% to 0.1% by weight of vitamin B9, 0.01% to 0.1% by weight of vitamin B12, and 24% to 80% by weight of a pharmaceutically acceptable carrier. The pharmaceutically acceptable carrier can be any one or any combination of plant-based oil, caprylocaproyl macrogolglycerides, polyoxyethylene castor oil or derivatives, polysorbate, polyglycerol esters of fatty acids, sucrose esters of fatty acids, polyethylene alkyl esters, polyoxyl 40 stearate and phospholipids. The composition may further comprise beeswax and/or butylated hydroxytoluene.

Furthermore, the present invention also provides the use of the composition disclosed herein in the manufacture of a medicament for preventing or mitigating dementia in a subject. Particularly, medicaments comprising the composition of the invention can be used to prevent, delay or mitigate memory deterioration and/or other mental abilities. The compositions provided herein can be formulated into solid dosage forms or liquid dosage forms. Preferably, the medicament is prepared in the form of capsules.

EXAMPLE

An example is provided below to illustrate different aspects and embodiments of the invention. The example is not intended in any way to limit the disclosed invention, which is limited only by the claims.

Example 1

10 mg beeswax and 1 mg butylated hydroxytoluene are melted in 152.7 mg vegetable oil at 70 to 75° C. and the mixture is cooled to about 50° C. Then, 50 mg caprylocaproyl macrogolglycerides, 50 mg polyoxyethylene castor oil derivatives and 152.7 mg vegetable oil are added to the mixture and mixed until a homogeneous mixture is obtained. Subsequently, 200 mg tocotrienols, 49 mg tocopherol, 36 mg squalene and 256.8 mg vegetable oil are added to the mixture and mixed well. 11.74 mg B vitamin powder is sieved through 60 mesh sieve and transferred into the mixture and mixed well. The final mixture is then sieved through a 60 mesh sieve prior to filling or encapsulation.

Example 2

20 mg beeswax and 1 mg butylated hydroxytoluene are melted in 528.5 mg vegetable oil at 70 to 75° C. and the mixture is cooled to about 50° C. Then, 75 mg caprylocaproyl macrogolglycerides and 75 mg polyoxyethylene castor oil derivatives are added to the mixture and mixed until a homogeneous mixture is obtained. Subsequently, 200 mg tocotrienol, 49 mg tocopherol and 20 mg squalene are added to the mixture and mixed well. 15.5 mg B vitamin powder is sieved through 60 mesh sieve and transferred into the mixture and mixed well. The final mixture is then sieved through a 60 mesh sieve prior to filling or encapsulation.

The invention claimed is:

1. A composition for preventing or mitigating dementia in a brain of a subject, comprising:
    alpha-tocotrienol in an amount ranging from 4% to 11% by weight of the composition;
    beta-tocotrienol in an amount ranging from 0.25% to 2% by weight of the composition;
    gamma-tocotrienol in an amount ranging from 7% to 15% by weight of the composition;
    delta-tocotrienol in an amount ranging from 2.0% to 7% by weight of the composition;
    alpha-tocopherol in an amount ranging from 3% to 9% by weight of the composition;
    squalene in an amount ranging from 1.0% to 5.0% by weight of the composition;
    vitamin B6 in an amount ranging from 1.0% to 1.5% by weight of the composition;
    vitamin B9 in an amount ranging from 0.04% to 0.06% by weight of the composition;
    vitamin B12 in an amount ranging from 0.03% to 0.05% by weight of the composition; and
    a pharmaceutically acceptable carrier in an amount ranging from 40% to 70% by weight of the composition;
    wherein administration of the composition reduces or prevents white matter lesions in the brain of the subject.

2. The composition according to claim 1, wherein the pharmaceutically acceptable carrier is selected from the group consisting of beeswax, butylated hydroxytoluene, plant-based oil, caprylocaproyl macrogolglycerides, polyoxyethylene castor oil or derivatives, polysorbate, polyglycerol esters of fatty acids, sucrose esters of fatty acids, polyethylene alkyl esters, polyoxyl 40 stearate, phospholipids and combinations thereof.

3. The composition according to claim 1, wherein the squalene is derived from a plant material.

* * * * *